US009345406B2

(12) United States Patent
Spencer et al.

(10) Patent No.: US 9,345,406 B2
(45) Date of Patent: May 24, 2016

(54) OCCLUSION-CROSSING DEVICES, ATHERECTOMY DEVICES, AND IMAGING

(71) Applicant: Avinger, Inc., Redwood City, CA (US)

(72) Inventors: Maegan K. Spencer, Menlo Park, CA (US); John B. Simpson, Woodside, CA (US); Stephen C. Davies, El Dorado Hills, CA (US)

(73) Assignee: Avinger, Inc., Redwood City, CA (US)

( * ) Notice: Subject to any disclaimer, the term of this patent is extended or adjusted under 35 U.S.C. 154(b) by 54 days.

(21) Appl. No.: 13/675,867

(22) Filed: Nov. 13, 2012

(65) Prior Publication Data

US 2013/0123615 A1 May 16, 2013

Related U.S. Application Data

(63) Continuation-in-part of application No. 13/433,049, filed on Mar. 28, 2012, now Pat. No. 8,644,913.

(60) Provisional application No. 61/559,013, filed on Nov. 11, 2011.

(51) Int. Cl.
| | | |
|---|---|---|
| *A61B 5/05* | (2006.01) | |
| *A61B 5/00* | (2006.01) | |
| *A61B 17/3207* | (2006.01) | |
| *A61B 5/02* | (2006.01) | |
| *A61B 19/00* | (2006.01) | |
| *A61B 6/12* | (2006.01) | |
| *A61B 6/00* | (2006.01) | |
| *A61B 17/22* | (2006.01) | |

(52) U.S. Cl.
CPC .............. *A61B 5/0066* (2013.01); *A61B 5/0062* (2013.01); *A61B 5/0084* (2013.01); *A61B 5/02007* (2013.01); *A61B 5/6852* (2013.01); *A61B 17/320758* (2013.01); *A61B 19/5225* (2013.01); *A61B 6/12* (2013.01); *A61B 6/487* (2013.01); *A61B 19/54* (2013.01); *A61B 2017/22068* (2013.01); *A61B 2019/5206* (2013.01); *A61B 2019/5217* (2013.01); *A61B 2019/5234* (2013.01); *A61B 2217/007* (2013.01); *A61B 2562/0233* (2013.01)

(58) Field of Classification Search
CPC combination set(s) only.
See application file for complete search history.

(56) References Cited

U.S. PATENT DOCUMENTS

| | | | |
|---|---|---|---|
| 4,178,935 A | 12/1979 | Gekhaman et al. | |
| 4,552,554 A | 11/1985 | Gould et al. | |

(Continued)

FOREIGN PATENT DOCUMENTS

| | | | |
|---|---|---|---|
| CN | 1875242 A | 12/2006 | |
| CN | 1947652 A | 4/2007 | |

(Continued)

OTHER PUBLICATIONS

Simpson et al.; U.S. Appl. No. 14/171,583 entitled "Occlusion-Crossing Devices, Imaging, and Atherectomy Devices," filed Feb. 3, 2014.

(Continued)

*Primary Examiner* — Long V Le
*Assistant Examiner* — Ellsworth Weatherby
(74) *Attorney, Agent, or Firm* — Shay Glenn LLP

(57) ABSTRACT

Described herein are methods for producing and identifying characteristic ("crescent shaped") regions indicative of an atherectomy plaque within a vessel, and systems and devices adapted to take advantage of this characteristic region.

9 Claims, 6 Drawing Sheets

(56) References Cited

U.S. PATENT DOCUMENTS

| | | |
|---|---|---|
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,771,774 A | 9/1988 | Simpson et al. |
| 4,841,977 A | 6/1989 | Griffith et al. |
| 4,926,858 A | 5/1990 | Gifford, III et al. |
| 5,000,185 A | 3/1991 | Yock |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,383,460 A | 1/1995 | Jang et al. |
| 5,383,467 A | 1/1995 | Auer et al. |
| 5,429,136 A | 7/1995 | Milo et al. |
| 5,431,673 A | 7/1995 | Summers et al. |
| 5,459,570 A | 10/1995 | Swanson et al. |
| 5,465,147 A | 11/1995 | Swanson |
| 5,556,405 A | 9/1996 | Lary |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,843,050 A | 12/1998 | Jones et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,643 B1 | 6/2003 | Gharibadeh |
| 6,575,995 B1 | 6/2003 | Hutler et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |

(56) References Cited

U.S. PATENT DOCUMENTS

| | | |
|---|---|---|
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fischer |
| 8,361,097 B2 | 1/2013 | Patel et al. |
| 8,548,603 B2 | 10/2013 | Swoyer et al. |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1* | 8/2005 | Maschke ............... 606/159 |
| 2005/0192496 A1 | 9/2005 | Maschke |
| 2005/0201662 A1 | 9/2005 | Petersen et al. |
| 2005/0222519 A1 | 10/2005 | Simpson |
| 2005/0222594 A1* | 10/2005 | Maschke ............... 606/159 |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander et al. |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |

(56) References Cited

U.S. PATENT DOCUMENTS

| | | |
|---|---|---|
| 2009/0244485 A1 | 10/2009 | Walsh et al. |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0274270 A1 | 10/2010 | Patel et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0040238 A1 | 2/2011 | Wulfman et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0263936 A1 | 10/2011 | He et al. |
| 2011/0301625 A1 | 12/2011 | Mauch et al. |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0253186 A1 | 10/2012 | Simpson et al. |
| 2012/0289971 A1 | 11/2012 | Segermark et al. |
| 2013/0138128 A1 | 5/2013 | Patel et al. |
| 2013/0296695 A1 | 11/2013 | Spencer et al. |
| 2015/0099984 A1 | 4/2015 | Kankaria |
| 2015/0126856 A1 | 5/2015 | Tachibana et al. |
| 2015/0141816 A1 | 5/2015 | Gupta et al. |
| 2015/0208922 A1 | 7/2015 | Simpson et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | 2002-214127 A | 7/2002 |
| JP | 2004-516073 | 6/2004 |
| JP | 2005-114473 A | 4/2005 |
| JP | 2005-249704 A | 9/2005 |
| JP | 2008-175698 A | 7/2006 |
| JP | 2006-313158 A | 11/2006 |
| JP | 2006-526790 | 11/2006 |
| JP | 2006-326157 A | 12/2006 |
| JP | 2007-225349 A | 9/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| KR | 2007/0047221 | 5/2007 |
| RU | 2185859 C2 | 7/2002 |
| RU | 2218191 C2 | 12/2003 |
| WO | WO 91/017698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO 2008/029506 A | 3/2008 |
| WO | WO 2008/042987 A2 | 4/2008 |
| WO | WO 2008/086613 A1 | 7/2008 |
| WO | WO 2008/087613 A2 | 7/2008 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO 2012/061935 A1 | 5/2012 |

OTHER PUBLICATIONS

He et al.; U.S. Appl. No. 14/019,466 entitled "Devices and Methods for Predicting and Preventing Restenosis," filed Sep. 5, 2013.

Aziz et al.; Chronic total occlusions—a stiff challenge requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Wang et al.; Common-path endoscopic Fourier domain OCT with a reference Michelson interferometer; Proceedings of the SPIE; vol. 7566; pp. 75660L-75660L-7; Jan. 2010.

Spencer et al.; U.S. Appl. No. 13/654,357 entitled "Atherectomy Catheters and Non-Contact Actuation Mechanism for Catheters," filed Oct. 17, 2012.

Gonzalo et al.; Optical coherence tomography patterns of stent restenosis; Am. Heart J.; 158(2); pp. 284-293; Aug. 2009.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Patel et al.; U.S. Appl. No. 13/929,579 entitled "Guidewire Positioning Catheter," filed Jun. 27, 2013.

Simpson et al.; U.S. Appl. No. 14/424,266 entitled "Re-entry stylet for catheter," filed Feb. 26, 2015.

Simpson et al.; U.S. Appl. No. 14/424,277 entitled "Balloon atherectomy catheters with imaging," filed Feb. 26, 2015.

* cited by examiner

OCCLUSION-CROSSING DEVICES, ATHERECTOMY DEVICES, AND IMAGING

CROSS REFERENCE TO RELATED APPLICATIONS

This application claims the benefit under 35 U.S.C. 119 of U.S. Provisional Patent Application No. 61/559,013, filed Nov. 11, 2011, titled "ATHERECTOMY METHODS AND DEVICES." This application is herein incorporated by reference in its entirety.

This application is also a continuation-in-part of U.S. patent application Ser. No. 13/433,049, filed Mar. 28, 2012, titled "OCCLUSION-CROSSING DEVICES, IMAGING, AND ATHERECTOMY DEVICES," now Publication No. US-2012-0253186-A1. This application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, methods and systems described herein are related to the treatment, identification, and removal of atheroma. In particular, described herein are systems, methods, devices and techniques for identifying distinguishing morphology in vessel images to direct or orient interventional devices.

BACKGROUND

Coronary artery disease is the leading cause of death within the United States for men and women. It is characterized by a buildup of material (often fatty) in the internal lumen of the coronary arteries. It is also associated with the hardening of the arterial walls. The buildup of material commonly starts on one side of the vessel and grows across the open lumen. As such, the last point of patency often occurs at the boundary between the material deposit (disease) and the healthy vessel.

Atherectomy is the process of removing diseased tissue from a stenosed lumen so as to restore patency and blood flow. There currently exist a number of devices that facilitate atherectomy. However, the operation of such devices has a number of shortcomings. In some instances, the active element of the atherectomy device acts equally in all directions, requiring the device to reside in the center of the diseased portion to maintain optimum efficacy. In other instances, the active element is directional but as such needs some method of visualization to orient the active element with respect to the diseased tissue. In many instances, the method of visualization that is employed is angiography, which is only capable of giving a silhouette of the open lumen.

Further, minimally invasive techniques for treating coronary artery disease, such as atherectomy, typically involve the placement of a guidewire through the occlusion prior to performing the atherectomy. For example, a chronic total occlusion (CTO) device can be used to place a guidewire through the occlusion and ultimately cross through the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

Moreover, minimally invasive surgical procedures to treat coronary artery disease depend on the precise positioning and manipulation of interventional devices. Guidance provided by high-resolution imaging can enable the characterization of tissue and lesion properties in vivo prior to treatment. As the majority of atherogenesis occurs in an eccentric fashion within the artery, therapeutic tools that have onboard imaging provide a distinct opportunity to selectively treat the diseased portion of a vessel. Even with on-board imaging techniques, however, it can be difficult to interpret the images so as to properly orient and steer the interventional devices as needed.

Accordingly, there is a need for a consistent and precise mechanism for steering or orienting occlusion-crossing, atherectomy, or other interventional devices. The invention described herein is based on the novel realization that a characteristic morphology (or morphological structure) may be visualized when (or after) passing a structure through the lumen of a vessel containing an atherectomy plaque mass (atheroma).

SUMMARY OF THE DISCLOSURE

The present invention relates to methods of forming and/or identifying characteristic morphologies within a vessel that indicate the presence, orientation and location of plaque masses within the vessel. Also described are devices to image, identify, and use this characteristic morphology (e.g., morphological structure) to orient a device, and/or remove or navigate the plaque in the peripheral or coronary vasculature.

In general, in one embodiment, a method of identifying an atherectomy plaque mass in a vessel includes applying circumferential radial force within the vessel to displace a rigid plaque mass and force the vessel wall to stretch away from the device; imaging the vessel to create an image; and identifying crescent-shaped structures associated with an atherectomy plaque in the image.

This and other embodiments can include one or more of the following features. The method can further include identifying the orientation of a plaque mass based on the directionality of the crescent-shaped structures. The method can further include identifying the position of a plaque mass relative to outer layered structures of a vessel wall based on the crescent-shaped structures. Imaging the vessel can include imaging the vessel with optical coherence tomography. The method can further include inserting a device into the vessel, and the device can apply the circumferential radial force. Imaging the vessel can include imaging with an imaging sensor attached to the device. The method can further include orienting the device within the vessel based on the crescent-shaped structures. Orienting the device can include pointing a directional cutter at a plaque mass identified based upon the crescent-shaped structure. Orienting the device can include directing the device based upon the relationship between markers in the image and the crescent-shaped structures. The method can further include rotating the imaging sensor to obtain the image.

In general, in another embodiment, a method of identifying an atherectomy plaque mass within a vessel includes the steps of: applying circumferential radial force within the vessel to displace a rigid plaque mass and forcing the vessel wall to stretch away from the device; visualizing the vessel wall following the application of circumferential radial force; and identifying crescent-shaped structures. The crescent-shaped structures may be formed by the application of circumferential radial force from within the lumen of the vessel.

This and other embodiments may include one or more of the following features. The method may also include the step of identifying the orientation of a plaque mass based on the directionality of the crescent-shaped structures. In some variations, the method may also include the step of identifying the position of a plaque mass relative to the outer layered structures of a vessel based on the crescent-shaped structures. In some variations, the method may also include the step of orienting a device or therapeutic tool within the vessel based on the crescent-shaped structures.

Any of the methods described herein can be carried out by a controller. Thus, an imaging system can be configured to detect, label, and/or highlight the characteristic morphological structures and/or use them to automatically detect or suggest the location of an atheroma.

In general, in one embodiment, an atherectomy device includes a distal end configured to dissect plaque from within a vessel. The device includes an elongate catheter body, a troweled distal tip extending from the catheter body and a rotatable cutter. The troweled distal tip has a curved outer surface configured to conform to an outer vessel and a scooped inner edge configured to at least partially plane along the plaque. The rotatable cutter is at least partially within the troweled distal tip.

This and other embodiments can include one or more of the following features. The device can further include an OCT sensor near or on the rotatable cylindrical cutter and configured to image radially into the vessel. The device can further include an inner lumen opening through the rotatable cutter into which material cut by the device may be driven. The rotatable cutter can be partially covered by the curved outer surface and can be partially exposed proximate to the scooped inner edge. The device can be configured to self-orient within the vessel.

In general, in another embodiment, an atherectomy device includes a distal end configured to dissect an atherectomy plaque using visual cues generated by a device with on-board optical coherence tomography, the device comprising: an elongate catheter body; a distal tip having a shaped opening (which may be a beveled opening, a trowel-shaped opening, or a tongue-shaped opening); a rotatable cylindrical cutter at least partially within the troweled or tongue-shaped opening; an OCT sensor near or on the rotatable cylindrical cutter and configured to image around the periphery of the catheter and into the vessel; and an inner lumen open through the rotatable cutter into which atherectomy material may be driven.

This and other embodiments can include one or more of the following features. The device may include a rotatable drive shaft for rotating the cutting element (cylindrical cutter) and/or the OCT sensor. Other elements may also or alternatively be included. In some variations, the distal tip is generally trowel or shovel-shaped in order to match the morphology of the plaque/wall interface revealed by the characteristic crescent shape described herein.

DETAILED DESCRIPTION

When crossing an occlusion of a blood vessel and imaging the vessel, such as with optical coherence tomography (OCT), an unexpected, yet predictable and characteristic morphology (or geometry) can be identified. The resulting characteristic morphology, described further herein, is formed at the boundary between the layered vessel wall structures and a plaque mass when crossing a chronic total occlusion (CTO) with a catheter or crossing device such as those described in: U.S. patent application Ser. No. 12/689,748, filed Jan. 19, 2010, titled "GUIDEWIRE POSITIONING CATHETER," now Publication No. US-2010-0274270-A1; U.S. patent application Ser. No. 12/108,433, filed Apr. 23, 2008, titled "CATHETER SYSTEM AND METHOD FOR BORING THROUGH BLOCKED VASCULAR PASSAGES," now U.S. Pat. No. 8,062,316; U.S. patent application Ser. No. 12/829,277, filed Jul. 1, 2010, titled "ATHERECTOMY CATHETER WITH LATERALLY-DISPLACEABLE TIP," now Publication No. US-2011-0004107-A1; U.S. patent application Ser. No. 12/829,267, filed Jul. 1, 2010, titled "CATHETER-BASED OFF-AXIS OPTICAL COHERENCE TOMOGRAPHY IMAGING SYSTEM," now Publication No. US-2010-0021926-A1; U.S. patent application Ser. No. 12/790,703, filed May 28, 2010, titled "OPTICAL COHERENCE TOMOGRAPHY FOR BIOLOGICAL IMAGING," now Publication No. US-2010-0305452-A1; U.S. patent application Ser. No. 13/175,232, filed Jul. 1, 2011, titled "ATHERECTOMY CATHETERS WITH LONGITUDINALLY DISPLACEABLE DRIVE SHAFTS," now Publication No. US-2012-0046679-A1; U.S. patent application Ser. No. 13/433,049, filed Mar. 28, 2012, titled "OCCLUSION-CROSSING DEVICES, IMAGING, AND ATHERECTOMY DEVICES," now Publication No. US-2012-0253186-A1, each of which is herein incorporated by reference in its entirety. The characteristic morphology may formed as a result of a dissection plane that is generated between a plaque mass and the lumen walls while traversing a vascular lesion, e.g., in peripheral and coronary CTO intervention.

As described herein, the resulting morphology is highly characteristic and can be used to obtain information with respect to the position of the disease within and with respect to the vessel. This information can also be utilized in real-time to orient the therapeutic portion of a device (e.g., atherectomy cutter or pre-shaped tip, etc.) toward disease and away from healthy tissue.

Using an imaging modality, such as optical coherence tomography (OCT), it is possible to visualize the shape or geometry that is created when advancing a device through a vascular lesion, such as a CTO. In some instances, the distinguishing shape or morphology that results when passing through a vascular lesion is a crescent-shaped feature (or a pair of such features) which may be formed around the circumference of the device, as shown in FIGS. 1-3.

Figure 1:
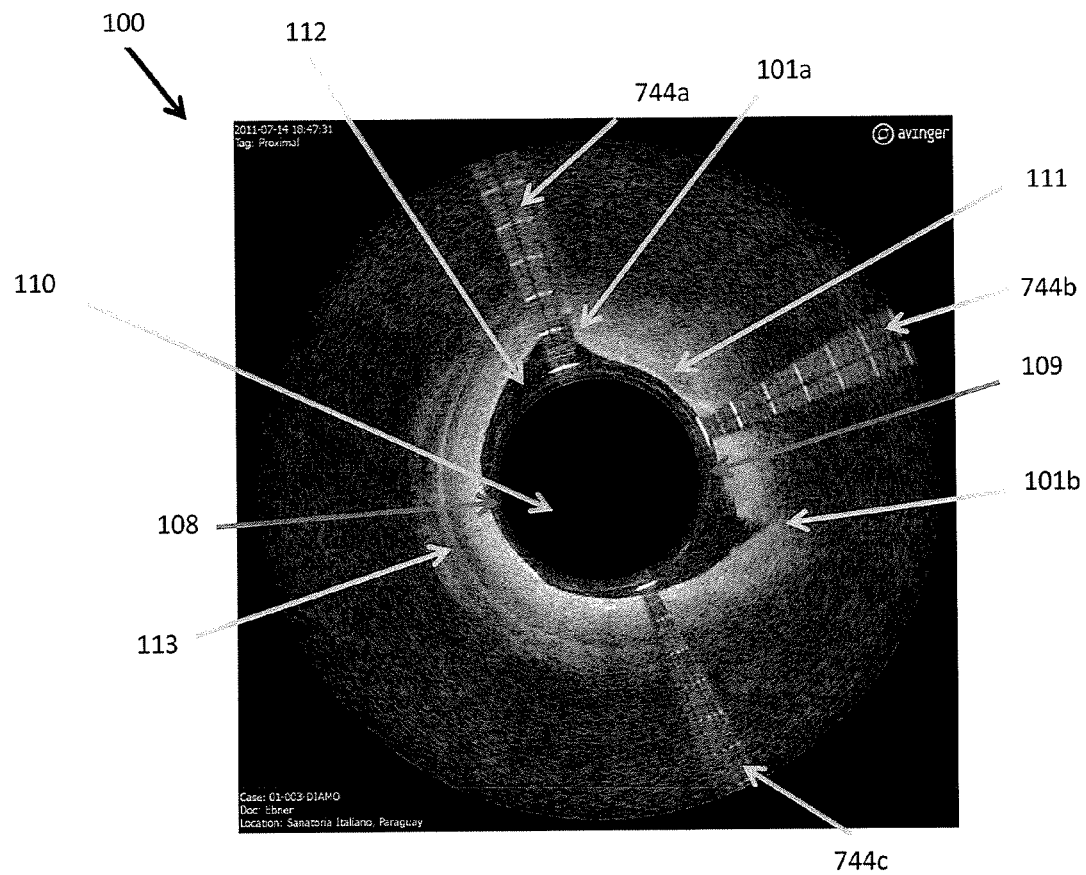
FIGS. 1-3 show examples of OCT images from within the lumen of a blood vessel, illustrating the crescent-shaped morphology described herein.
Figure 2:
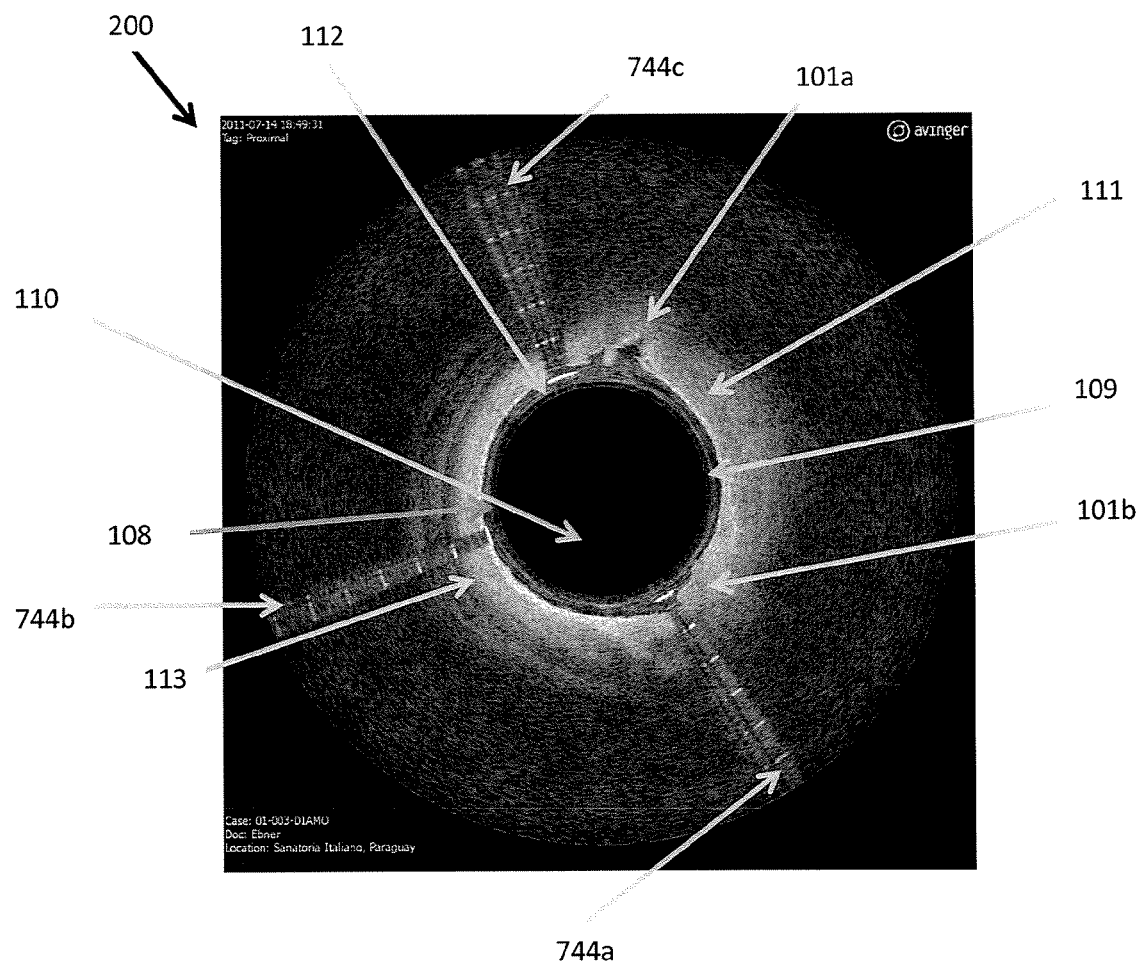
Figure 3:
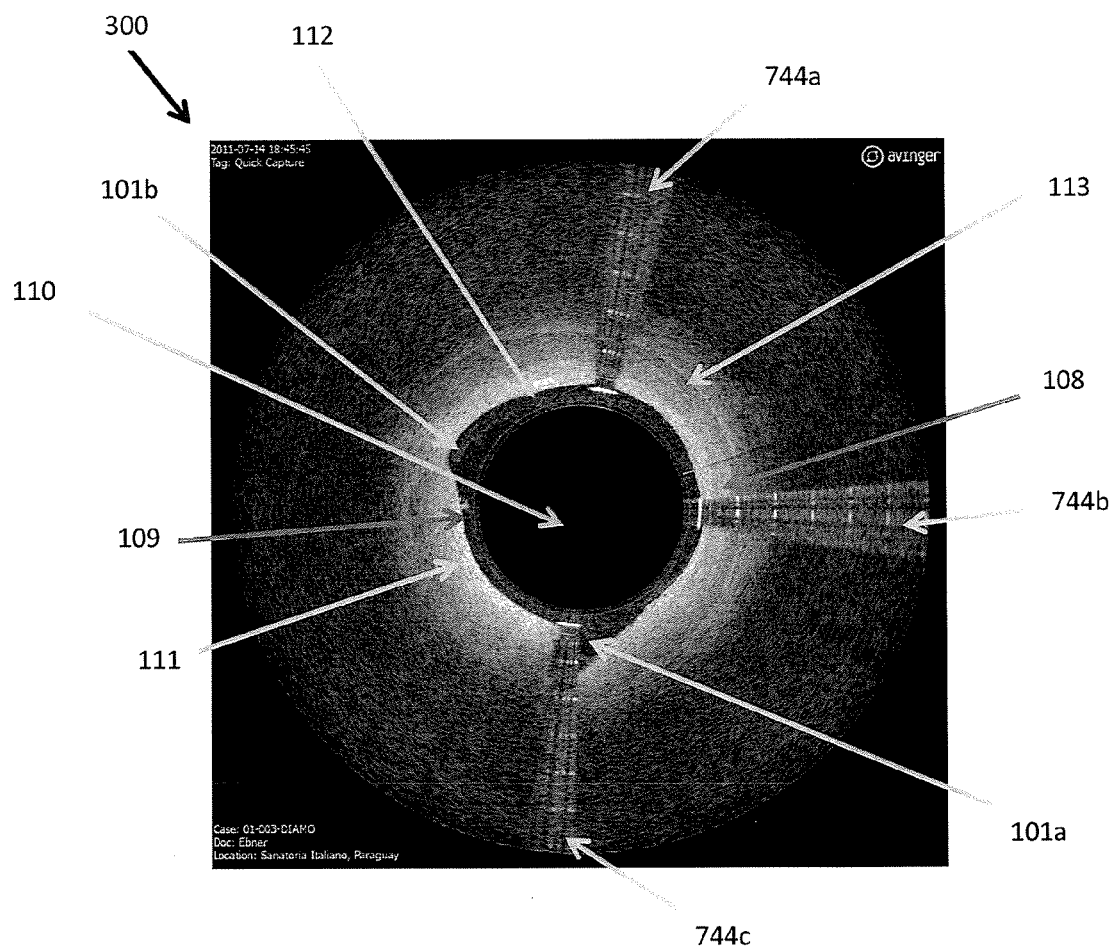

In FIGS. 1-3, the images are gathered by an occlusion-crossing catheter having a rotatable distal tip which allows the tip to be driven past the occluded region. The images in FIGS. 1-3 are generated by rotating an OCT imaging sensor around the lumen of the vessel. The tip of the catheter may be rotated both (or either) clockwise or counterclockwise. The rate of rotation may be constant or variable, and may be between about 1 and about 5000 rpms. The OCT imaging sensor may be located on the catheter (e.g., at or near the distal end), and the sensor may be rotated to enable circumferential imaging of the lumen (by rotating an end portion of the catheter, for example). The catheter may be held in a relatively fixed position within the lumen of the vessel or it may be moved longitudinally through the lumen while obtaining the images.

For example, FIG. 1 shows an OCT image taken from a catheter equipped to take OCT images from within a lumen of a vessel that is at least partially occluded. In this example, a catheter (which may include the OCT imaging catheter) has been inserted past the occluded region shown. In FIG. 1, the tip of the catheter has already passed through this occluded region of the vessel, and OCT image 100 was taken of the vessel after passage of the tip.

The image 100 shown includes a black circle 110, which is representative of the device itself. Around the black circle 110 extends a dark portion 112. The dark portion 112 forms a semi-circular-like shape (or a "D" shape) with a rounded portion 108 on one side and a substantially linear portion 109 on the other side (note that the substantially linear portion is shorter than the rounded portion 108 and can be slightly bowed in the opposite direction). The rounded portion 108 and the substantially linear portion 109 meet in characteristic crescents or "crescent wings" 101a, 101b (in this image 100 at the 11 and 4 o'clock positions, respectively) to give a "cat ear" shaped profile. The crescent wings 101a, 101b point inwards (towards the substantially linear portion 109) to frame an amorphous structure 111 indicating a plaque mass in the vessel. In contrast, the rounded portion 108 lies against layered structures 113 of different contrast, indicating healthy tissue of the vessel (e.g., intima, adventitia, media).

Although the inventions described herein are not bound by any particular theory, the characteristic morphology of bracketing crescents ("cat ears") shown and described with respect to FIG. 1 is may be primarily due to the tendency for a device inserted within the vessel to track along the side of a plaque mass (between the plaque mass and the vessel wall) rather than through the plaque mass. As the device tracks along the side of the plaque mass, the wall of the vessel stays intact and stretches, thereby bowing out in a substantially circumferential manner along with the device (forming the rounded portion 108). In contrast, the plaque mass may undergo little, if any, stretching, thereby maintaining a substantially straight profile (forming the substantially linear portion 109). The dark portion 112 may be formed as blood is cleared by flushing through a lumen on the device or peripheral apparatus. The pointed portion of the crescent wings 101a, 101b may form as a result of the healthy tissue stretching around the cylindrically-shaped device, which is positioned between the plaque mass and the vessel outer wall (e.g., adventitia). Further, the black circle 110 is a feature that is added (e.g., by software) into the image to indicate the approximate shape and location of the device relative to the environment; the OCT sensor in this example does not image within the device itself.

Thus, the characteristic morphology described with respect to FIG. 1 may be mainly due to the tendency for a device placed within a clogged vessel to track along the side of a plaque mass. The morphology along this path may promote anisotropic stretching around the device. When circumferential radial forces are applied in this space, the rigid plaque mass is less likely to accommodate the introduced device, forcing the more compliant vessel wall to preferentially stretch away from the device. When visualized with onboard imaging, this morphology appears as crescent-shaped edges, with wings (crescent edges) that occur on each side of a plaque region. These wings (also referred to as crescents or cat ears) are typically bowed in one direction, forming a half-moon shape, as shown in FIG. 1. The directionality of these wings may be indicative of the position of a plaque mass relative to the outer layered structures of a vessel, e.g., the smaller side of the shape may be on the side of the plaque region. This shape is consistent with predications based on the relative compliance of vessel wall structures and disease.

Additional representative OCT images 200, 300 are also shown in FIGS. 2 and 3. Each image 200, 300 includes the same or similar characteristic morphology as described with respect to FIG. 1. The images 100, 200, and 300 all show the morphology in a slightly different orientation (for example, the crescent wings 101a, 101b are in the 11 o'clock and 4 o'clock positions in image 100 and the crescent wings 101a, 101b in the 6 o'clock and 10 o'clock positions in the FIG. 300). The second crescent shape in FIG. 2 101b is partially hidden behind the reference structure 744a. This difference in orientation between the images is a result of the varying nature of disease within a vessel and is dependent on the path that a CTO-crossing device takes while traversing through a lesion. This orientation may actively change while traversing a device through a diseased segment of a vessel.

The characteristic morphology shown in FIGS. 1-3 can be used as a marker to provide a real-time roadmap during an interventional procedure in diseased vasculature to aid in device placement. That is, the crescent-shaped characteristic features, with a plaque mass on one side and layered wall structures on the other, can be used as a clear guide during interventional procedures in the peripheral or coronary vasculature.

Further, the tip of an atherectomy and/or imaging device (including, for example, the cutting element or occlusion-crossing element) can be repositioned toward a plaque mass using the crescent morphology as a guide, enabling a device to track along the true lumen of a CTO and avoid perforation of the vessel. A therapeutic tool may also be positioned using this feature to remove or modify a plaque mass and avoid the outer wall structures of a vessel, preventing vessel perforation.

In one embodiment, marker features (e.g., fiducial markers) on the device can assist in aligning the device in the desired orientation relative to the crescent morphology. The markers can be configured to obstruct imaging from the OCT sensor at least once per rotation of the rotatable tip. For example, the markers on the device can be a radiopaque material (e.g., a metal) that can be seen in high contrast during fluoroscopy or a material that reflects or absorbs optical beams from the OCT system (e.g., metal, dense polymer, carbon powder). As described in more detail below, the imaging system may also be configured to identify, mark, and/or highlight these characteristic crescent morphological shapes and to display them as real-time markers. Other markers may also be shown by the imaging system, including makers displayed on the image that indicate the radial orientation of the device, structures in the tissue, etc. For example, markers may be overlaid on the image to achieve a similar result to physical markers on the catheter (e.g., electrically, magnetically, or in software). In some variations, a marker can be aligned with a distinguishing feature of the inserted device (e.g., catheter), such as a fixed jog or exposed cutter, to aid in steering or cutting with the device.

Figure 5:
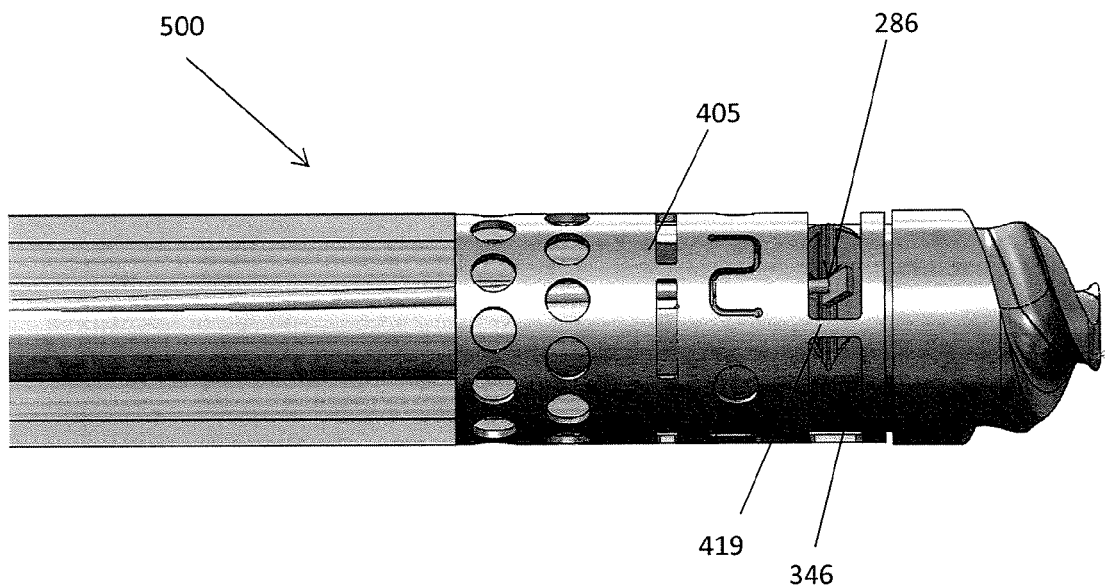
FIGS. 5 and 6 illustrate an exemplary device with markers configured to display on an OCT image.
Figure 6:
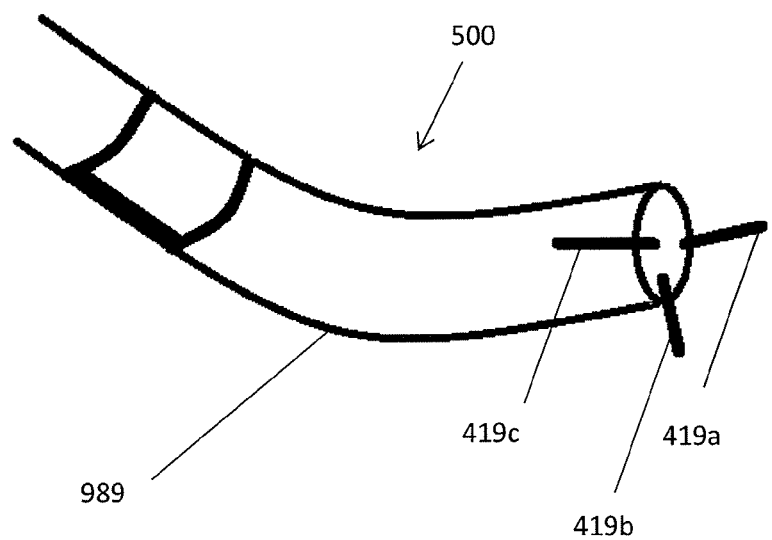

For example, as shown in FIG. 5, an occlusion-crossing device 500 can include a chassis 405 having three window regions 346 separated by spines 419 (which may be referred to as posts, struts, dividers, separators, etc.) arranged annularly around the chassis 405. These spines 419 may serve as reference markers as the imaging sensor 286 rotates and views the tissue through the windows 346. For example, spines may produce reference regions 744a, 744b, and 744c such as those shown in FIGS. 1-3. In some embodiments, as shown in FIG. 6, the spines 419 can be aligned relative to a jog 989 in the device (here such that the middle spine 419b is aligned opposite to the jog direction 989). This relative orientation can assist in pointing the jog and thus the end of the device in the desired direction.

The markers can thus produce corresponding reference regions in the images. Thus, in FIGS. 1-3, reference regions 744a, 744b, 744c in the form of striped rays indicate the locations of the markers or spines 419a, 419b, 419c, respectively, on the device 500. The reference regions 744a, 744b, 744c can thus indicate the orientation of the distal end of the catheter within the body.

During a CTO procedure, one goal may be to steer the catheter towards the plaque or unhealthy tissue. Because the middle spine 419b is aligned opposite to the jog 989 (as shown in FIG. 6), the ray 744b corresponding to the middle spine 419b can be oriented opposite to the non-healthy tissue or plaque 111 (indicated by the substantially linear portion 109 between the crescent wings 101a, 101b) to steer the catheter in the correct direction. FIG. 1 shows the catheter deflected toward the layered, healthy tissue. FIG. 2 shows the catheter rotated such that it is deflected toward the unhealthy, non-layered structure.

Thus, the system may be configured to allow the orientation of the catheter to be rotated into the correct position using fixed directional markers and the characteristic crescent wing morphology of the OCT images. It is to be understood that, although the images 100, 200, 300 are described as resulting from using a device similar to the occlusion-crossing device 500 that other device designs can be steered using the same morphology (for example, devices having different reference markers).

The crescent morphology described here can also provide direct, real-time feedback during an interventional procedure for general device repositioning based on the thickness of the layered wall structures, helping prevent perforation of the vessel. For example, the crescent morphology may indicate a plaque, however if the nearby layered wall structures appear to be very thin and perivascular structures can be seen in the OCT images beyond the layered structures, it is possible that the vessel is close to being perforated. In this case, the OCT image may serve as a warning sign, and the physician may pull the device proximal to reposition for a different approach.

An imaging system, and particularly an OCT imaging system as described, may be configured to detect, label, and/or highlight the crescent-shaped morphological structures in an image, and/or use them to automatically detect or suggest the location of an atheroma. For example, an imaging system may include a controller configured to automatically identify the crescent-shaped morphology within the OCT images. In some variations, this analysis is done separately from the imaging system (e.g., either concurrent or in real-time, or later, including as a post-procedure analysis). Likewise, in some embodiments, a controller can be configured to orient or steer a device through the vessel based upon images showing the characteristic crescent-shaped morphology. Standard image-processing algorithms may be used or adapted for use to identify the characteristic pair of crescents, which typically occur from the lumen of the vessel, radiating outward into the vessel wall. An imaging and/or image-processing system may execute (e.g., as executable code, firmware, software, hardware, etc.) image analysis logic that can determine if the crescent-shaped morphological structures are present in an image and/or indicate that they are present on the image. For example, analysis logic may determine if the structures are present in an OCT image, and may also identify them in any appropriate manner, e.g., by marking, etc. Likewise, the imaging and/or image-processing system may execute image analysis logic that can determine the direction in which the crescent-shaped structures point and, thus, the location of an atheroma therebetween.

Figure 7:
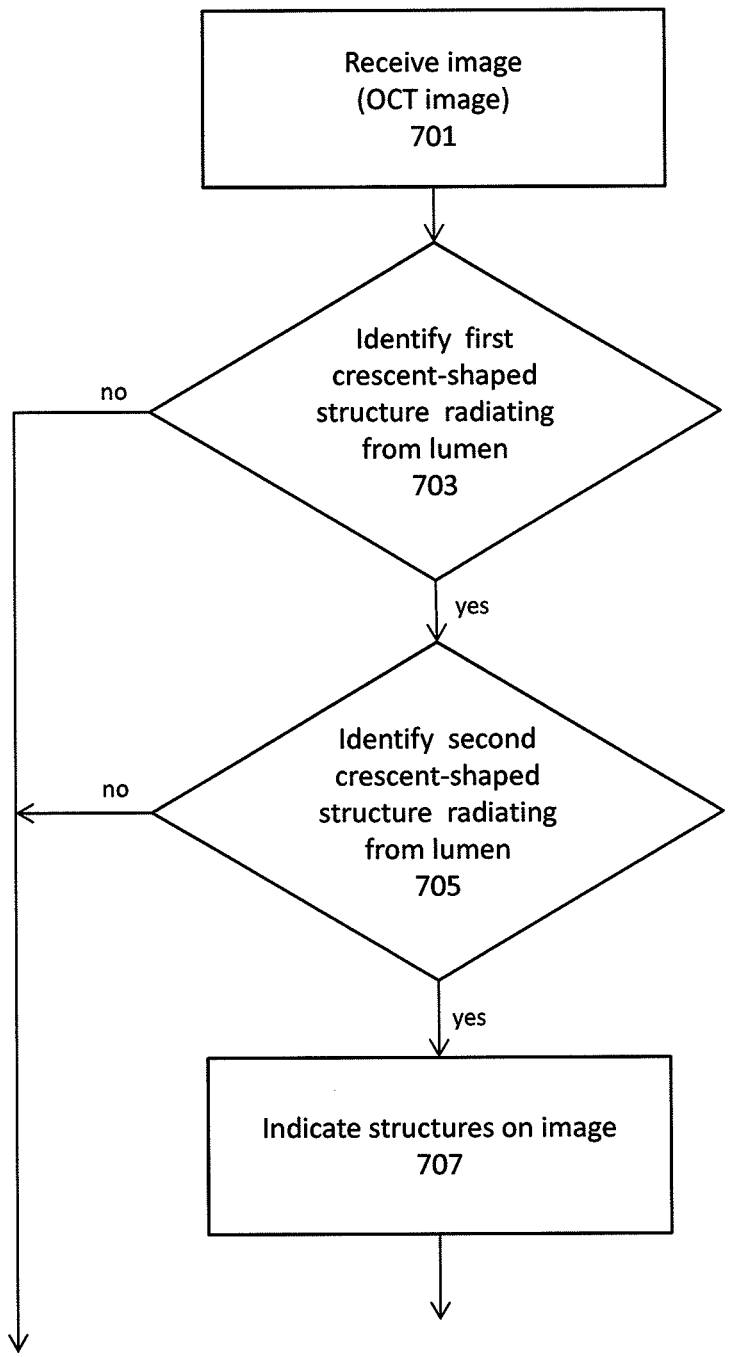
FIG. 7 illustrates one method of detecting crescent-shaped structures indicative of the boundaries of an atheroma as described herein.

FIG. 7 shows a schematic of one variation of a method of implementing an automatic detection of the crescent-shaped structures as discussed above. At step 701, an image, such as an OCT image, from within an anatomical lumen is obtained. At step 703, it can be determined whether there is a crescent-shaped structure radiating from the lumen in the image. If so, then it can be determined at step 705 whether there is a second crescent-shaped structure radiating from the lumen in the image. If so, then, at step 707, the first and second crescent-shaped structures can be used to identify anatomical structures within the lumen, such as a plaque mass and/or healthy tissue within the lumen.

Devices or systems, including atherectomy devices and/or systems, can be designed to take advantage of the morphology resulting from the crossing of the lesion and the previously unsuspected ability to reliably determine atheroma using these newly-recognized morphological markers. For example, a device may include a pre-shaped tip region that slides easily along/between the crescent shaped morphology. Thus, a therapeutic tool may take a shape that fits into the form factor provided by this morphology, facilitating advancement through a lesion, treatment of a plaque mass, and/or delivery of a therapeutic agent (e.g., pharmaceutical).

Thus, a device can utilize the shape that is formed at the boundary between the healthy vessel and the disease when the open lumen is distended by a dissection device. The device can utilize a form factor which matches that of the dissection that is observed at the interface between the disease and the healthy vessel. The profile of the tip of the device is formed into the crescent shape described above.

Figure 4:
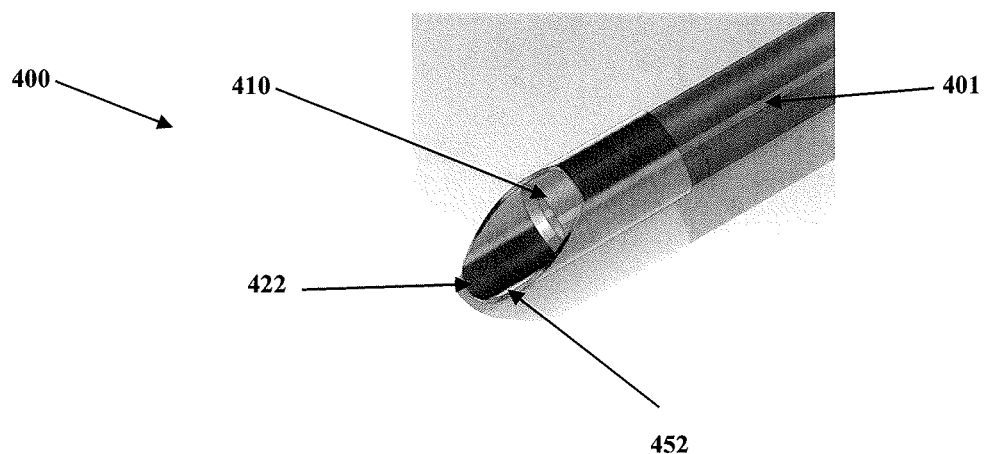
FIG. 4 illustrates one variation of an atherectomy device adapted as described herein.

For example, referring to FIG. 4, in one variation, the distal end of an atherectomy device 400 having a rotating cutter may be adapted to take advantage of the characteristic morphology of the vessel. As shown in FIG. 4, the atherectomy device can include an elongate catheter body 401 and a rotatable cutter 410 near the distal end of the catheter body 401. The elongate body can end in a beveled tip 422 (i.e. with a troweled or tongue-shaped opening) that extends distally past the rotatable cutter 410 on one side of the cutter 410 and proximal of the rotatable cutter 410 on the other side of the cutter 410. The troweled or tongue-shaped tip 422 is thus configured to protect a portion of the rotatable cutter 410 while the exposed portion of the cutter 410 is configured to be placed in the cleft of the crescent. The troweled or tongue-shaped tip 422 has an outer curved surface configured to slide along the healthy tissue of the vessel wall and a scooped inner edge 452 configured to at least partially plane along the lesion. Thus, referring to FIGS. 1-3, the outer curved surface is configured to be placed against the rounded portion 108 and the proximal end of the scooped inner edge 452 is configured to plane between the cat ears 101a, 101b. Such a configuration would thus place the cutter 410 against the substantially linear portion 109.

In one embodiment, the cutter 410 can be actuated by a hollow drive cable which also acts to capture and store the material that is excised from the interior of the vessel. The drive cable can reside in the lumen of the catheter body. Further, in one embodiment, an optical fiber can run through the drive cable. The distal end of the optical fiber can be mounted on the cutter. The optical fiber can thus run from the cutter to the proximal connector of the device. The proximal connector provides a way to both optically and mechanically couple the fiber and drive cable to the system driving the device. The optical fiber can provide a way to generate an image of the cross-section of the vessel via OCT.

The device 400 can be easily redirected based on features apparent in the OCT image, such as this crescent wing morphology, by promoting a blunt dissection along which the tip 422 of the device 400 will track. The orientation of the device can be adjusted via visual cues generated by the OCT, such as the crescent wings. The final orientation of the device can be defined by the conformance of the shape of the tip 422 of the device 400 with the dissection plane, as described above. Advancing the device 400 pushes the cutter 410 into the linear section visible in the OCT image that is indicative of diseased tissue. In doing so, the disease region may be excised and forced into the hollow center of the drive cable. Further advancing of the device 400 pushes more disease into the cutter 410. Continuing the distal movement of the device to the distal point of the stenosis creates a patent lumen facilitating blood flow and the passage of a wire or other adjunct device past the disease. Removal of the drive cable/cutter assembly from the center of the device during the procedure would facilitate using the device sheath as an exchange or delivery catheter.

The device described herein has several advantages. For example, the device facilitates atherectomy in the coronary vasculature via image-guided cutting. Moreover, it offers a safe way to perform the procedure by orienting the device such that the tip 422 protects the healthy vessel wall from damage by the cutter.

In addition to a device having a pre-shaped tip configured to conform to the crescent-shaped tissue morphology described above, in some embodiments a device can be configured to self-orient through the vessel. In other words, the outer curved surface could automatically align with the healthy, stretched outer tissue layers (e.g., adventitia) while the beveled edge and thus the cutter could automatically align with the occlusion. In some embodiments, therefore, the device may not require an imaging sensor.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. A method of identifying a plaque mass within a vessel, the method comprising:
    inserting a device into the vessel, the device applying a force on the vessel to cause the vessel wall to stretch away from the device;
    imaging the vessel to create an image;
    identifying a location and orientation of a plurality of pointed crescent-shaped structures extending radially from a substantially semi-circular central portion in the image, the substantially semi-circular central portion having a substantially rounded portion and a substantially linear portion, each pointed crescent-shaped structure extending from a junction of the substantially rounded portion and the substantially linear portion; and
    determining a position of the plaque mass within the vessel relative to the device based upon the identified location and orientation of the pointed crescent-shaped structures in the image.

2. The method of claim 1, wherein imaging the vessel comprises imaging the vessel with optical coherence tomography.

3. The method of claim 1, wherein imaging the vessel comprises imaging with an imaging sensor attached to the device.

4. The method of claim 3, further comprising orienting the device within the vessel based on the location and orientation of the crescent-shaped structures.

5. The method of claim 4, wherein orienting the device comprises pointing a directional cutter of the device at the position of the plaque mass.

6. The method of claim 4, wherein orienting the device comprises directing the device based upon the relationship between markers in the image created by a portion of the device and the location and orientation of the crescent-shaped structures.

7. The method of claim 3, further comprising rotating the imaging sensor to obtain the image.

8. The method of claim 1, wherein identifying a location and orientation of a plurality of pointed crescent-shaped structures comprises determining which direction a tip of each crescent-shaped structure points.

9. The method of claim 8, wherein determining a position of the plaque mass comprises identifying a location between two pointed crescent-shaped structures in which the tips of the two pointed crescent-shaped structures point towards one another.

* * * * *